United States Patent

Brackett et al.

[11] Patent Number: 6,015,401
[45] Date of Patent: Jan. 18, 2000

[54] METHODS FOR VESSEL CANNULATION

[76] Inventors: Jacqueline Darlene Brackett, 8700 Dawes Lake Rd., Mobile, Ala. 36619; Fred Brackett, 8255 Brackett La., Semmes, Ala. 36575

[21] Appl. No.: 09/066,032

[22] Filed: Apr. 24, 1998

Related U.S. Application Data

[60] Continuation of application No. 08/605,280, Feb. 7, 1996, abandoned, which is a division of application No. 08/104,346, Aug. 9, 1993, Pat. No. 5,520,657.

[51] Int. Cl.[7] .................................................. A61M 5/00
[52] U.S. Cl. .......................... 604/506; 604/158; 604/191; 600/575
[58] Field of Search .................................. 600/575, 578; 604/89, 90, 158, 159, 163, 164, 173, 177, 191, 239, 51–53, 500, 506, 508, 168

[56] References Cited

U.S. PATENT DOCUMENTS

| | | |
|---|---|---|
| Re. 32,974 | 7/1989 | Porat et al. . |
| 2,626,604 | 1/1953 | Nadeau . |
| 3,097,646 | 7/1963 | Scislowicz . |
| 3,677,448 | 7/1972 | Harris, Sr. et al. . |
| 3,739,778 | 6/1973 | Frederick et al. . |
| 3,749,084 | 7/1973 | Cucchiara ............. 604/239 X |
| 3,766,916 | 10/1973 | Moorehead et al. . |
| 3,851,647 | 12/1974 | Monestere, Jr. et al. . |
| 3,859,998 | 1/1975 | Thomas et al. . |
| 4,188,949 | 2/1980 | Antoshkiw . |
| 4,243,034 | 1/1981 | Brandt . |
| 4,245,635 | 1/1981 | Kontos . |
| 4,245,654 | 1/1981 | Raitto . |
| 4,274,408 | 6/1981 | Nimrod . |
| 4,313,440 | 2/1982 | Ashley . |
| 4,327,723 | 5/1982 | Frankhouser . |
| 4,515,592 | 5/1985 | Frankhouser . |
| 4,529,399 | 7/1985 | Groshong et al. . |
| 4,610,665 | 9/1986 | Matsumoto et al. . |
| 4,613,329 | 9/1986 | Bodicky . |
| 4,685,904 | 8/1987 | Krebs . |
| 4,737,150 | 4/1988 | Baeumle et al. . |
| 4,767,407 | 8/1988 | Foran . |
| 4,813,938 | 3/1989 | Raulerson . |
| 4,957,637 | 9/1990 | Cornell . |
| 4,978,334 | 12/1990 | Toye et al. . |
| 5,045,065 | 9/1991 | Raulerson . |
| 5,246,426 | 9/1993 | Lewis et al. . |
| 5,257,979 | 11/1993 | Jagpal . |
| 5,279,570 | 1/1994 | Dombrowski et al. . |

(List continued on next page.)

FOREIGN PATENT DOCUMENTS

| | | |
|---|---|---|
| 0 056 103 | 7/1982 | European Pat. Off. . |
| 369 619 | 5/1990 | European Pat. Off. . |
| 583 052 | 2/1994 | European Pat. Off. . |
| 2004771 | 11/1969 | France . |
| 25 07 119 | 2/1976 | Germany . |
| 2 229 374 | 9/1990 | United Kingdom . |

OTHER PUBLICATIONS

"Safer Jugular Vein Cannulation: Recognition of Arterial Puncture and Preferential use of the External Jugular Route", by Jobes et al, Anesthesiology, pp. 535–355, 1983.

*Primary Examiner*—Wynn Wood Coggins
*Assistant Examiner*—A. T. Nguyen
*Attorney, Agent, or Firm*—Lena I. Vinitskaya; Guy L. Cumberbatch

[57] ABSTRACT

A syringe is disclosed having a large syringe housing which can be fitted with a large needle holder which in turn holds a large introducer needle. The introducer needle defines a passageway. A small seeker needle which is designed to fit within and through the passageway of the large introducer needle is attached by way of a small needle holder to a small syringe housing. A washer adapter attaches to the front of the small needle holder in order to have the small syringe housing move within a large syringe housing as a plunger for the large syringe housing. The small syringe housing in turn receives on one end a small syringe plunger which may define a small plunger lumen or chamber which can be used for transduction. Another embodiment has a modified needle having a port in the shaft within the syringe to allow sampling.

29 Claims, 5 Drawing Sheets

U.S. PATENT DOCUMENTS

| | | |
|---|---|---|
| 5,290,244 | 3/1994 | Moonka . |
| 5,322,518 | 6/1994 | Schneider et al. . |
| 5,328,480 | 7/1994 | Melker et al. . |
| 5,352,215 | 10/1994 | Thome et al. . |
| 5,354,285 | 10/1994 | Mazurik et al. . |
| 5,358,490 | 10/1994 | Henry et al. . |
| 5,368,574 | 11/1994 | Antonacci et al. . |
| 5,373,855 | 12/1994 | Skrabal et al. . |
| 5,380,290 | 1/1995 | Makower et al. . |
| 5,512,052 | 4/1996 | Jesch ................................... 604/164 X |
| 5,520,657 | 5/1996 | Sellers et al. . |
| 5,531,255 | 7/1996 | Vacca . |
| 5,562,633 | 10/1996 | Wozencroft . |
| 5,613,663 | 3/1997 | Schmidt et al. . |

FIG. 5

METHODS FOR VESSEL CANNULATION

RELATED APPLICATIONS

The present application is a continuation of Ser. No. 08/605,280, filed Feb. 7, 1996, now abandoned, which is a divisional of Ser. No. 08/104,346, filed Aug. 9, 1993, now U.S. Pat. No. 5,520,657, issued May 28, 1996.

BACKGROUND OF THE INVENTION

This invention applies to cannulation.

More particularly the invention applies to cannulation of the venous or arterial system but it is not limited to these sites.

PRIOR ART

Several devices for percutaneous sheathing introduction and several methods of cannulation are known in the art. Some of these involve transduction. Transduction is loosely defined as obtaining an electronic signal from a physical fluid pulse. The Seldenger technique is the most common method for introducing the catheter into a vein or artery. In this technique the vessel is located with a seeker needle (usually 22 g) and syringe and then an introducer needle is placed alongside in an attempt to access the same vessel. A wire is then placed through the needle and the needle is removed. The catheter is threaded into the vessel while being guided by the wire. Once the catheter is in place the wire is removed. One problem associated with the Seldenger technique, particularly with central venous cannulation, is that insertion is largely a learned technique which requires the maintenance of the angle of insertion of the introducer needle along the same plane as the seeker needle. Failure to maintain the same angle as the seeker needle may result in misplacement of the introducer needle or failure to locate the vessel.

The presented devices and associated techniques eliminate the need for two puncture sites by allowing for the insertion of a larger needle over a smaller needle while using the same needle—syringe unit. These devices and the associated techniques prevent unnecessary bleeding, allow the maintenance of the angle for insertion of the larger needle, and allow for appropriate insertion of the introducer needle.

Therefore it is a purpose of this invention is to provide an improved method of cannulation.

It is the further purpose of the invention to provide a novel device and method for insertion of a larger needle over a seeker needle.

A further purpose is to provide an improved method for sampling while performing cannulation and for maintaining a needle angle while performing cannulation.

These and other objects and advantages of the invention will become better understood hereinafter from a consideration of the specification with reference to the accompanying drawings forming part thereof, and in which like numerals correspond to parts throughout the several views of the invention.

SUMMARY OF THE INVENTION

The invention is an improved and safe method for cannulation utilizing a unique syringe device which allows for the insertion of a seeker and introducer needle as one unit. This provides the user with the ability to aspirate through both lumens independently or simultaneously. The preferred embodiment utilizes a unique and improved hypodermic syringe wherein a smaller (seeker) hypodermic syringe acts as a plunger for the larger (introducer) hypodermic syringe. The smaller syringe is specially modified to allow aspiration through a seeker needle and, if necessary, transduction of the same needle through the modified plunger of the small syringe. The large syringe barrel then acts as a unit with the introducer needle, advancing it over the seeker needle. This device allows one to use the small syringe and needle unit to inject local anesthetic, locate the correct vessel and aspirate with a seeker needle, transduce the needle holder in order to have the small syringe housing move within a large syringe housing as a plunger for the large syringe housing. The small syringe housing in turn receives on one end a small syringe plunger which may define a small plunger lumen or chamber which can be used for transduction. Another embodiment has a modified needle having a port in the shaft within the syringe to allow sampling.

BRIEF DESCRIPTION OF THE DRAWINGS

For a further understanding of the nature and objects of the present invention, reference should be made to the following detailed description taken in conjunction with the accompanying drawings in which like parts are given like reference numerals and wherein.

DETAILED DISCUSSION OF THE PREFERRED EMBODIMENT(S)

The method of cannulation of a vessel and device described herein describes a process comprising the steps of (a) determining the angle of insertion;

(b) inserting a seeker needle 5 mounted on a housing barrel 2 at the determined angle of insertion into the vessel;

(c) transducing or aspirating the seeker needle 5 once it has accessed the vessel in question (either method being generally acceptable with transducing being more certain);

(d) maintaining the angle of the seeker needle 5 while inserting the introducer needle 4;

(e) inserting an introducer needle 4 over the seeker needle 5 while maintaining substantially the extent of penetration of the seeker needle 5;

(f) aspirating the seeker needle 5 after inserting the seeker needle;

(g) aspirating or transducing the introducer needle 4 after inserting the introducer needle 4 into the vessel over the seeker needle 5;

(h) removing the seal 3 from the plunger 11 to the housing barrel 2; and (i) removing the plunger 11.

Figure 1:
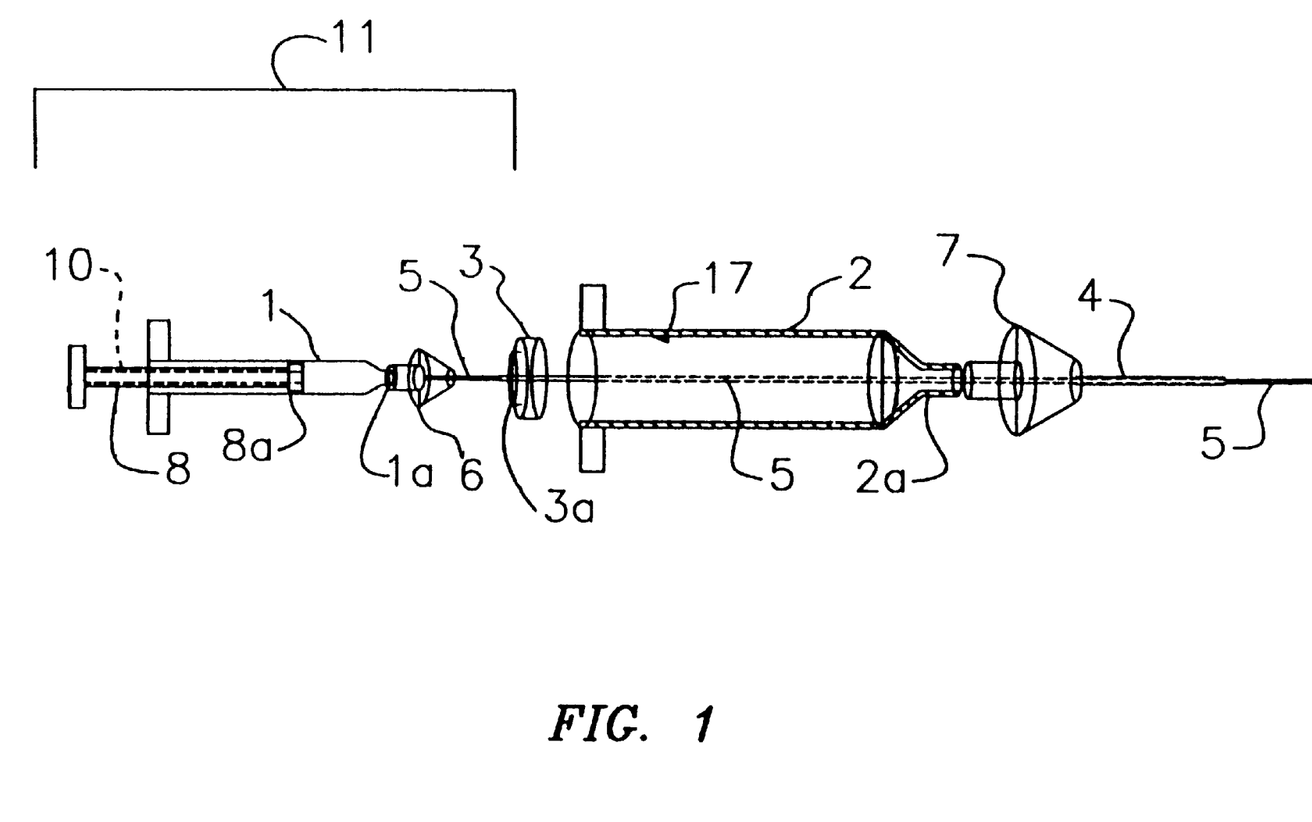
FIG. 1 is a plan view of the preferred embodiment of the invention.

As can best be seen by reference to FIG. 1, the invention in the preferred embodiment comprises a large syringe housing 2 which can be fitted with a large needle holder 7 which in turn, holds an introducer (large) needle 4. The introducer needle 4 defines a passageway 9 (seen in an alternative embodiment in FIG. 2). A seeker (small) needle 5 which is designed to fit within and through the passageway 9 of the large introducer needle 4 is attached by way of small needle holder 6 to a small syringe housing 1. A washer adapter 3 attaches to the front of the small needle holder 6 in order to have the small syringe housing 1 move within the large syringe housing 2 as a plunger for the large syringe housing 2.

Figure 4:
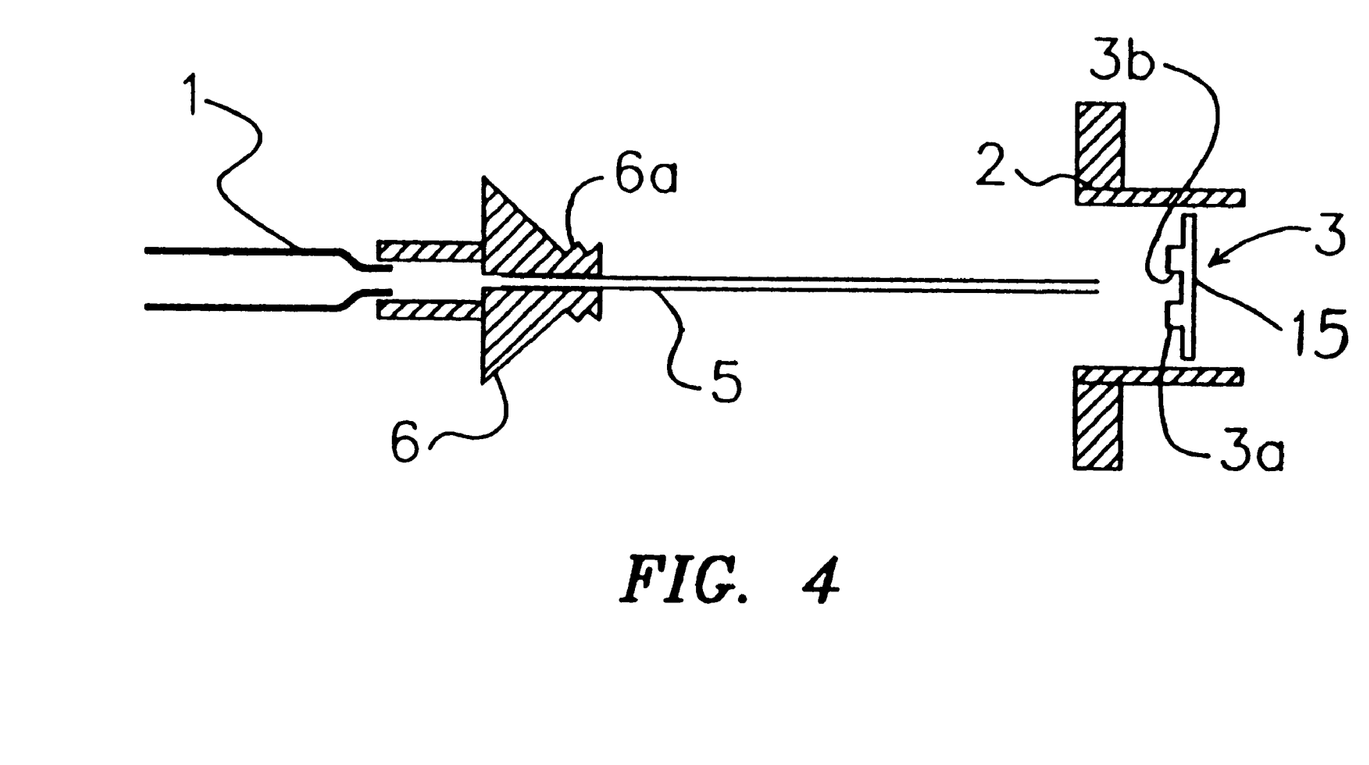
FIG. 4 is a detail of the modified washer seal of FIG. 3.

The small syringe housing 1 in turn receives on one end a small syringe plunger 8 having a plunger seal 8a. The plunger 8 may define a small plunger lumen or chamber 10 which can be used for transduction. For transduction, a transducer needle (not shown) could pass through the lumen 10 of the small plunger 8 and then into the appropriate vessel. The front end 1a of the small syringe housing 1 receives seeker needle holder 6 which holds the seeker needle 5. The seeker needle holder 6 holds the seal or washer 3. As shown on FIG. 4, the needle holder 6 may define threads 6a to screw into threads 3b defined on a bolt 3a attached to or formed out of an extension of washer 3. Similarly washer 3 may be made of suitable material so that it forms a solid puncturable unit which may reseal when the small needle 5 is removed.

The length of the small needle 5 is sufficient so that, when the large hypodermic plunger 11 comprised of the washer 3 and the syringe housing 1 is inserted a desired distance into the large housing 2, a sufficient length of the small needle 5 extends beyond the end of large needle 4 so that it may be used as a seeker needle 5.

The seeker needle 5 is properly inserted into the vessel (e.g. vein, artery or other fluid containing body of the body) into which the large needle 4 will ultimately be inserted using techniques known in the art.

Figure 2:
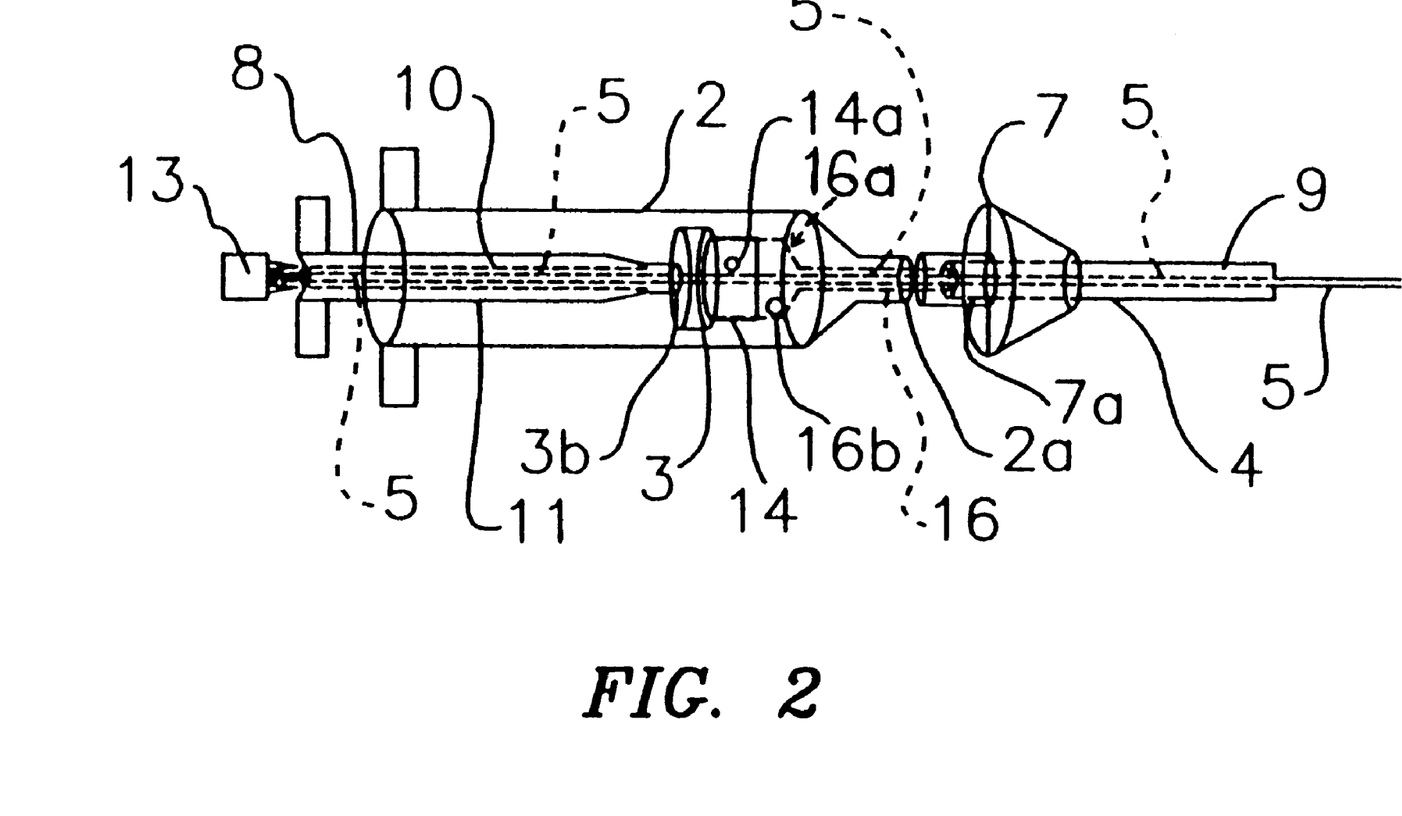
FIG. 2 is an alternate embodiment showing the use of a modified needle in place of the double syringe technique shown in FIG. 1.

Through either withdrawing plunger 11 to sample or through transduction utilizing opening 10 it can be determined that the seeker needle 5 is in the right location. For transduction it may be necessary to extend a current carrying wire into the opening 10 and contacting the needle 4 or 5 to be transduced. In FIG. 2 an extension of the seeker needle 5 serves this purpose. All this can be done while maintaining the angle of the seeker needle 5 because of the inclusion of the sampling syringe housing 1 in the plunger 11 of the large syringe housing 2 which holds the introducer needle 4.

When it is determined that the angle is correct and the seeker needle 5 is in the desired vessel, the large plunger housing 2 can be moved forward while the small plunger housing 1 is held in place. As the large housing 2 is moved forward and the plunger 11 is held in place, needle 4 is inserted over seeker needle 5 without moving the seeker needle 5 forward. The seeker needle 5 may be marked by color or otherwise to mark the length held within the patient to help insure the seeker needle 5 does not go further into the patient during insertion.

Continued aspiration or transduction is possible during this process to assure penetration is properly maintained.

When necessary, the large needle holder 7 can be removed from the housing 2 and the seeker needle completely withdrawn and replaced as necessary or the small plunger 11 may be removed with the needle 5 from the large housing 2 with or without the seal 3 to accomplish the same result.

Figure 3:
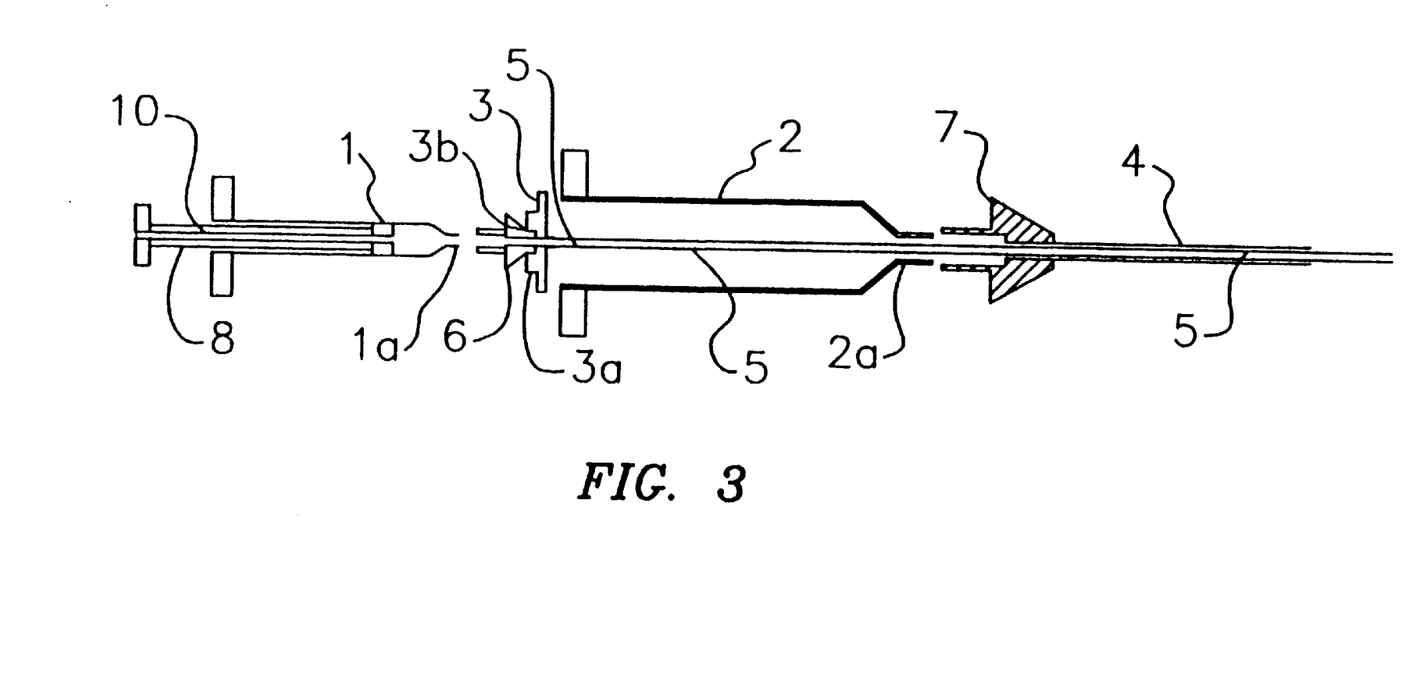
FIG. 3 is a cross section view of the invention of FIG. 1 having a modified washer seal.

A point is marked on the large housing 2 at which point the introducer needle 4 has been moved forward to completely cover the seeker needle 5. This is the point of full insertion. In the preferred embodiment this point may be preserved by a triangular stop 17 defined by housing 2 which is sloped to allow seal 3 to pass but presents a straight barrier to halt the backward movement of seal 3. As shown in more detail in FIG. 3 and 4, it may be desirable to remove all of the plunger 11 except the seal 3 from housing 2.

The invention in FIG. 1 comprises two plungers which advance or withdraw the two needles independently of each other to allow correct placement while allowing sampling or introduction of solution from either needle 4 or 5. This is all accomplished through one entry site instead of the most common technique now used in which there is more than one puncture site and the angle of insertion is often impossible to maintain due to anatomical movement and related difficulties.

This invention allows for less blood loss and a substantially lower number of puncture sites; thereby reducing the possibility of infection, nerve injury, pneumothorax, hematomas and other well known complications of venous or arterial cannulation.

A 22 gauge needle is used as the seeker needle 5 to find the vessel, then an 18 gauge or larger introducer needle 4 is threaded over the seeker needle 5.

Although the introducer needle 4 is typically a standard type of needle, this could easily be any type of device such as a fiber optic cable or housing for receiving fiber optics.

In the preferred embodiment shown in FIG. 1, the smaller needle 5 is a 22 gauge needle which would extend approximately one and one quarter inches beyond the 18 gauge tip as a seeker needle 5 when plunger 11 is fully inserted into housing 2.

FIG. 2 shows an alternate embodiment with a single housing 2 and without housing 1. Luer lock 13 holds a seeker needle 5 within the plunger 11 and would come out of an opening 10 in the rear of the plunger 11. If the plunger 11 is held in place, the introducer needle 4 which is usually an 18 gauge needle may be inserted over the seeker needle 5 without changing the position of the seeker needle 5.

The seal or washer 3 of the large syringe plunger 11 may be designed to lock in place within housing 2 by a lock 17 between the housings. The seal 3 may be unscrewed from the needle housing 6. By having a hemostasis valve 15 defined by the seal 3 which valve closes the blood flow when the seeker needle 5 is withdrawn, the introducer needle 4 may be left in place while syringe housing 1 is removed leaving the seal 3 in place for testing purposes (e.g. checking for a spurt of blood into the housing 2. This blood spurt would be kept within housing 2 by the seal 3 which would close up when the seeker needle 5 was withdrawn).

The housing barrel 2 would be used to push the introducer needle 4 down over the seeker needle 5 when positive testing for venous blood by transduction or sampling confirms venous access. The cap or lock 13 covering the small plunger lumen 10 may be removed in order to transduce the needle 4 or 5 in the fashion similar to that discussed for the prior art.

FIG. 2 shows an embodiment with a single plunger 11. As shown in FIG. 2, the needle 5 may pass through the opening or lumen 10 in the plunger 11. The holding means or luer lock 13, usually a screw-on attachment to the rear of the plunger 8 acts to hold the small needle 5 in place. The needle 5 may be removed while the plunger 11 remains in place within the housing 2 by pulling out the luer lock 13 with the needle 5 attached.

The larger needle 4 is typically an 18 gauge needle. In the embodiment shown in FIG. 2 the 18 gauge needle attaches to the large housing 2 at the housing end 2a by way of the large needle holder 7.

The introducer needle 4 then fits over a secondary needle 16 which is slightly larger than the introducer needle 4 and is thereby designed to tightly receive the introducer needle 4. A needle opening 16b in an enlarged portion 16a of the secondary needle 16 serves to allow blood to be collected within the large housing as the plunger 11 is withdrawn creating a vacuum in the area between the front of the housing 2a and seal 3.

The secondary needle 16 is held by a secondary holder 14 to the plunger 11 in front of the plunger seal 3. A holder hole 14a defined by the secondary holder 14 allowing the secondary needle 16 to communicate with the interior of the housing 2 could be used for the same purpose and as an alternative to the needle opening 16b.

In the alternative embodiment of FIG. 2, the seeker needle 5 would need to be long enough to fit through the plunger 11 and barrel 2 and 18 gauge introducer needle 4 in order to be used as a seeker.

In the embodiment shown in FIG. 2 the introducer needle 4 can be separated by removing the introducer needle holder 7 so that the housing 2 can be removed after insertion.

Figure 5:
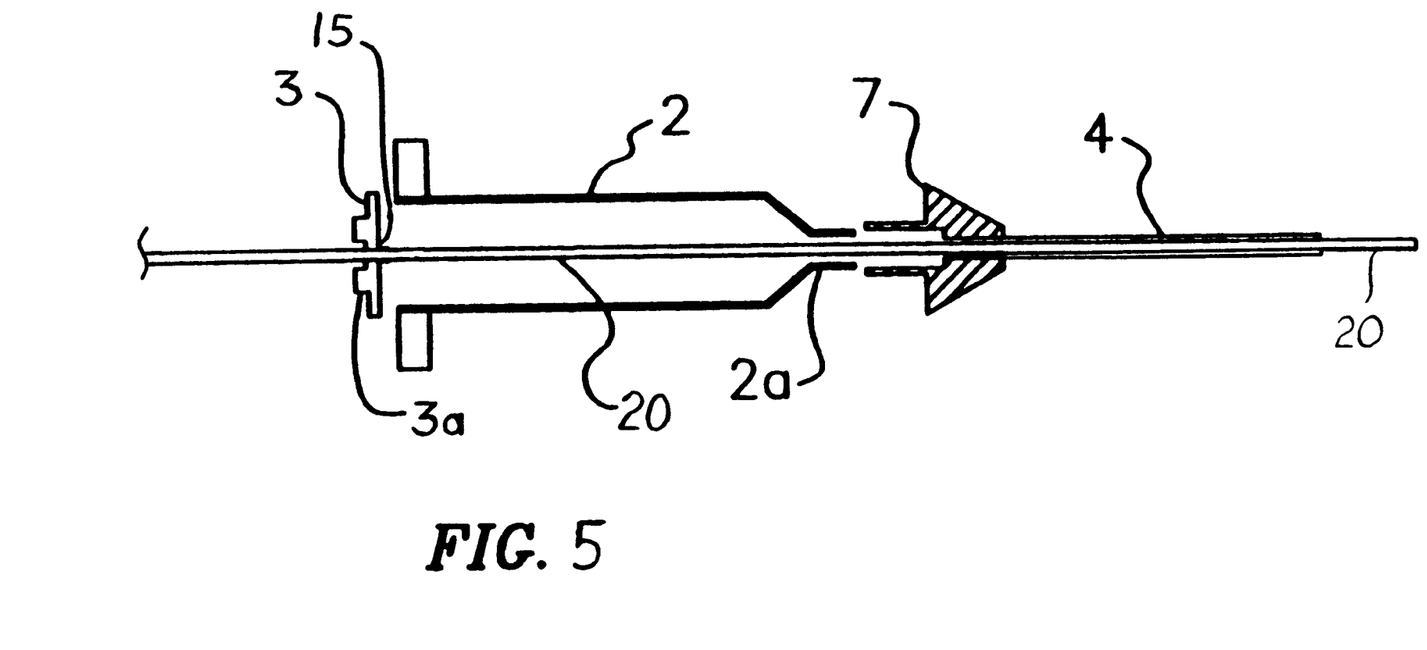
FIG. 5 is a plan view of the embodiment of FIG. 3 with a small syringe removed and an elongate element extending therethrough.

FIG. 5 illustrates an elongate element extending through hemostasis valve 15, and through the introducer needle 4 into a vessel (not shown). Such an elongate element 20 may be a rigid transduction needle, or a flexible guidewire in a modification to the Seldinger technique, as described in the background section.

We claim:

1. A method of cannulation of a vessel utilizing an introducer needle telescoped over a seeker needle, comprising:

inserting a hollow seeker needle into the vessel;

aspirating fluid through the seeker needle to verify that the seeker needle is in the vessel; and advancing the introducer needle over the seeker needle into the vessel.

2. The method of claim 1, wherein the step of inserting comprises advancing the hollow seeker needle together with the introducer needle.

3. The method of claim 2, wherein the introducer needle is attached to a syringe body, and the hollow seeker needle extends through a bore of the introducer needle into the barrel of the syringe body and is secured therein, and wherein the step of advancing the seeker needle together with the introducer needle comprises advancing the syringe body.

4. The method of claim 3, wherein the hollow seeker needle attaches to a second syringe body that is positioned within the barrel of the first syringe body, and wherein the step of aspirating fluid through the seeker needle comprises withdrawing a plunger within the second syringe body.

5. The method of claim 4, wherein the second syringe body is removably fastened to a seal and functions as a plunger for the first syringe body, the method further including aspirating fluid through the introducer needle to verify that the introducer needle is in the vessel during the step of the advancing the introducer needle over the seeker needle.

6. The method of claim 5, further including detaching the second syringe body from the seal after verifying that the introducer needle is in the vessel, and withdrawing the hollow seeker needle and second syringe body from the introducer needle and first syringe body.

7. The method of claim 6, wherein the seal includes a hemostasis valve, the method further including advancing an elongate element through the hemostasis valve and through the introducer needle into the vessel.

8. The method of claim 1, wherein the hollow seeker needle attaches to a syringe body and the method includes injecting a local anesthetic to the area of cannulation using the syringe body and seeker needle prior to inserting the seeker needle into the vessel.

9. The method of claim 1, wherein the introducer needle attaches to a first syringe body and the seeker needle attaches to a second syringe body positioned within a chamber formed within the first syringe body, and wherein the step of aspiration comprises withdrawing a plunger positioned within the second syringe body.

10. The method of claim 9, wherein the second syringe body is removably fastened to a seal and functions as a plunger for the first syringe body, the method further including aspirating fluid through the introducer needle into the chamber to verify that the introducer needle is in the vessel during the step of advancing the introducer needle over the seeker needle.

11. The method of claim 1, wherein the seeker needle attaches to a syringe body and the step of aspirating fluid through the seeker needle comprises withdrawing a plunger positioned within the syringe body.

12. The method of claim 11, wherein the introducer needle attaches to a large syringe having a chamber which receives the syringe body attached to the seeker needle, and wherein the syringe body attached to the seeker needle includes a seal within the chamber to function as a plunger, the method further including aspirating fluid through the introducer needle into the chamber to verify that the introducer needle is in the vessel during the step of advancing the introducer needle over seeker needle.

13. The method of claim 12, wherein the syringe body and seeker needle are detachable from the seal, the method further including removing the syringe body and seeker needle from the large syringe after verifying that the introducer needle is in the vessel.

14. The method of claim 13, wherein the seal includes a hemostasis valve, the method further including advancing an elongate element through the hemostasis valve and through the introducer needle into the vessel.

15. The method claim 1, further including aspirating fluid through the introducer needle to verify that the introducer needle is in the vessel.

16. The method of claim 15, wherein the step of aspirating fluid through the introducer needle occurs during the step of advancing the introducer needle over the seeker needle.

17. A needle-over-a-needle method of cannulation of a vessel, comprising:

positioning a hollow smaller needle within a hollow larger needle so that the smaller needle extends from a distal tip of the larger needle;

advancing both the smaller needle and larger needle together into a patient;

penetrating the vessel with the smaller needle;

aspirating fluid through the smaller needle to verify penetration of the smaller need into the vessel;

advancing the larger needle over the smaller needle until the larger needle also penetrates the vessel; and withdrawing the smaller needle from within the larger needle.

18. The method of claim 17, further including aspirating fluid through the larger needle to verify penetration of the larger needle into the vessel.

19. The method of claim 17, further including advancing an elongate element into the vessel through the larger needle after withdrawing the smaller needle.

20. The method claim 17, wherein the step of aspirating fluid through the smaller needle comprises:

(a) attaching the smaller needle to a syringe; and (b) withdrawing fluid from the smaller needle into the syringe.

21. The method claim 17, wherein the step of penetrating a vessel with the smaller needle comprises transducing the smaller needle to determine proper penetration.

22. The method of claim 17, wherein the step of advancing the larger needle to penetrate the vessel comprises transducing the larger needle to determine proper penetration.

23. The method of claim 17, wherein the larger needle attaches to a first syringe body and the smaller needle attaches to a second syringe body positioned within a chamber formed within the first syringe body, the step of aspirating fluid through the smaller needle comprising withdrawing a plunger positioned within the second syringe body to verify penetration of the smaller needle into the vessel.

24. The method of claim 23, wherein the second syringe body is removably fastened to a seal and functions as a plunger for the first syringe body, the method further including aspirating fluid through the larger needle into the chamber to verify that the introducer needle is in the vessel during the step of advancing the introducer needle over the seeker needle.

25. A method of cannulation of a vessel, comprising:
preparing a dual-syringe for cannulation of the vessel, the dual-syringe including a larger syringe having an introducer needle extending distally therefrom, and a smaller syringe positioned within the barrel of the larger syringe and having a seeker needle extending distally therefrom through the introducer needle to project distally from a tip of the introducer needle;

advancing the dual-syringe until the seeker needle penetrates a vessel;

aspirating fluid from the vessel through the seeker needle to verify that the seeker needle has penetrated the vessel;

advancing the introducer needle over the seeker needle until the introducer needle penetrates the vessel; and retracting the smaller syringe and seeker needle from within the larger syringe and introducer needle.

26. The method of claim 25, further including aspirating fluid from the vessel through the introducer needle to verity that the introducer needle has penetrated the vessel.

27. The method of claim 25, wherein the smaller syringe is coupled to a seal and functions as a plunger within the barrel of the larger syringe, the method further including decoupling the smaller syringe from the seal prior to retracting the smaller syringe so that the seal remains within the larger syringe barrel.

28. The method of claim 13, wherein the seal comprises a hemostasis valve, the method further including passing an elongate element through the hemostasis valve and introducer needle after retracting the smaller syringe and seeker needle.

29. The method of claim 28, further including aspirating fluid from the vessel through the introducer needle to verify that the introducer needle has penetrated the vessel.

* * * * *